(12) United States Patent
Shimizu et al.

(10) Patent No.: US 9,011,893 B2
(45) Date of Patent: Apr. 21, 2015

(54) ALUMINUM HYDROXIDE PIGMENTS HAVING IMPROVED COLORING CAPABILITY

(71) Applicants: Katsumi Shimizu, Pomfret Center, CT (US); Shoji Takekawa, Shrewsbury, MA (US)

(72) Inventors: Katsumi Shimizu, Pomfret Center, CT (US); Shoji Takekawa, Shrewsbury, MA (US)

(73) Assignee: U.S. Cosmetics Corporation, Dayville, CT (US)

( * ) Notice: Subject to any disclaimer, the term of this patent is extended or adjusted under 35 U.S.C. 154(b) by 33 days.

(21) Appl. No.: 13/676,447

(22) Filed: Nov. 14, 2012

(65) Prior Publication Data
US 2014/0134215 A1    May 15, 2014

(51) Int. Cl.
*A01N 25/26*    (2006.01)
*A61K 8/02*    (2006.01)
*A61Q 1/04*    (2006.01)
*A61Q 1/06*    (2006.01)
*A61Q 1/08*    (2006.01)
*A61Q 1/10*    (2006.01)
*A61Q 15/00*    (2006.01)
*A61Q 17/04*    (2006.01)
*A61Q 19/10*    (2006.01)

(52) U.S. Cl.
CPC . *A61K 8/022* (2013.01); *A61Q 1/04* (2013.01); *A61Q 1/06* (2013.01); *A61Q 1/08* (2013.01); *A61Q 1/10* (2013.01); *A61Q 15/00* (2013.01); *A61Q 17/04* (2013.01); *A61Q 19/10* (2013.01)

(58) Field of Classification Search
None
See application file for complete search history.

(56) References Cited

U.S. PATENT DOCUMENTS

| | | | |
|---|---|---|---|
| 4,084,983 A * | 4/1978 | Bernhard et al. | ............. 106/402 |
| 4,309,480 A | 1/1982 | Armanini | |
| 4,323,554 A | 4/1982 | Bernhard | |
| 4,968,351 A | 11/1990 | Ahmed et al. | |
| 5,156,889 A | 10/1992 | DeLuca, Jr. | |
| 6,015,456 A | 1/2000 | Fukuda et al. | |
| 6,416,573 B2 | 7/2002 | Horino et al. | |
| 6,531,524 B2 | 3/2003 | Ring et al. | |
| 6,630,019 B2 | 10/2003 | Pike et al. | |
| 7,531,184 B2 | 5/2009 | Horino et al. | |
| 7,682,604 B2 | 3/2010 | Ogawa et al. | |
| 2001/0005735 A1 | 6/2001 | Ring et al. | |

FOREIGN PATENT DOCUMENTS

JP    2008088317 A    4/2008

* cited by examiner

*Primary Examiner* — Carlos Azpuru
(74) *Attorney, Agent, or Firm* — Pillsbury Winthrop Shaw Pittman LLP

(57) ABSTRACT

The embodiments relate to cosmetic compositions providing high coloring pigment particles capable of achieving high color coverage with less pigment. The compositions of embodiments include aluminum hydroxide particles coated with at least one pigment, and having an average coated ratio of from about 20% to about 100% pigment by weight of aluminum hydroxide, and a cosmetically acceptable carrier. The compositions may be useful as a foundation and/or as a composition to correct skin discoloration.

10 Claims, 1 Drawing Sheet

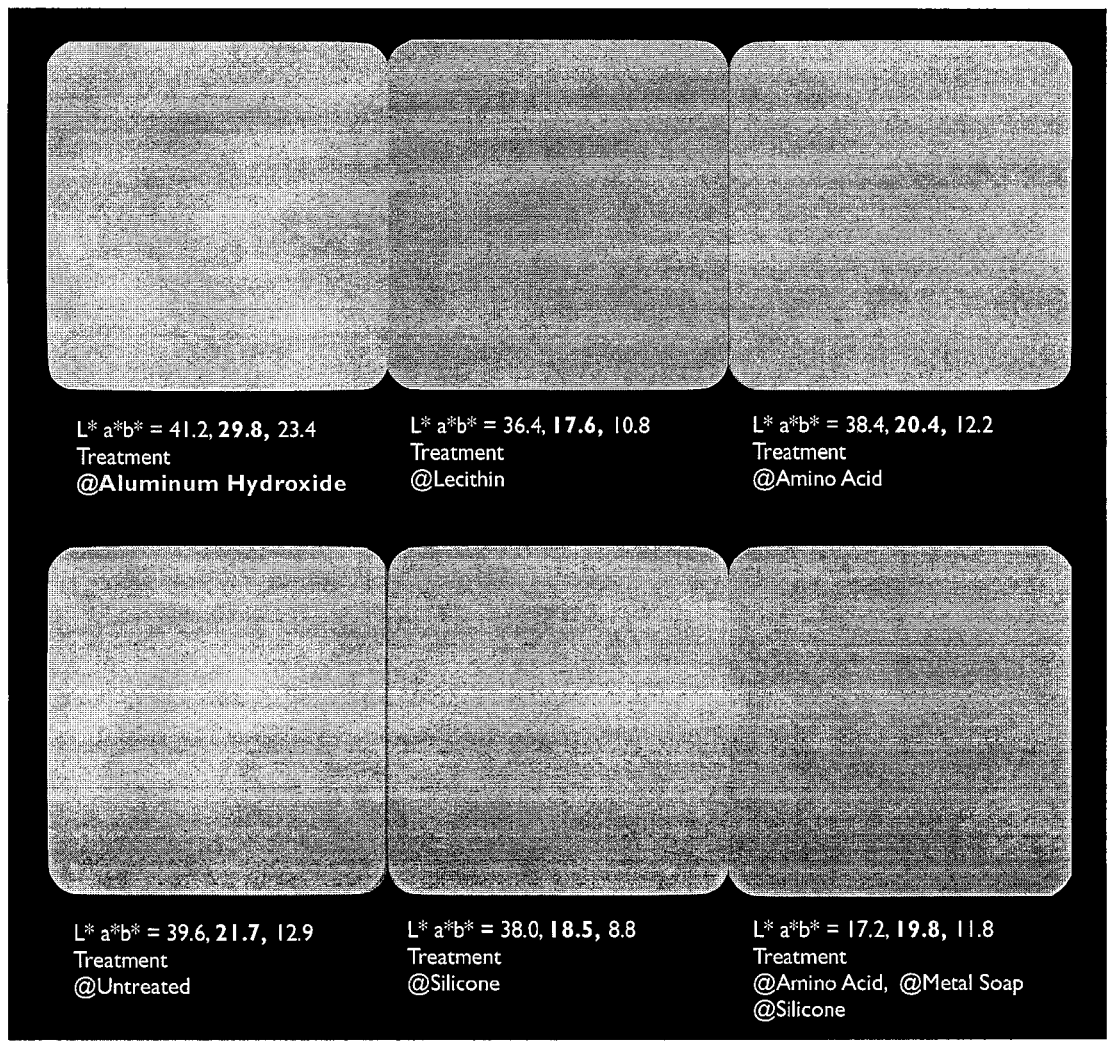

US 9,011,893 B2

ALUMINUM HYDROXIDE PIGMENTS HAVING IMPROVED COLORING CAPABILITY

FIELD OF THE INVENTION

The embodiments relate to cosmetic compositions providing a high coverage to the skin while retaining a natural skin appearance, in which the compositions include pigment-containing aluminum hydroxide particles and a cosmetically acceptable carrier. The compositions may be useful as a foundation and/or as a composition to correct skin discoloration, and may be used to cover skin imperfections while at the same time retaining a natural skin appearance.

BACKGROUND

Cosmetic compositions are used by consumers for regulating the condition of the skin and/or for improving the appearance of the skin. Cosmetic compositions, such as foundations, are popular amongst consumers, because they are capable of masking skin imperfections and skin tonal, variations—this ability is referred to as "coverage." These compositions also may provide coloration to the skin by incorporating conventional metal oxide pigments into the compositions, such as iron oxide pigments and titanium dioxide and other powder. Cosmetic compositions also are popular amongst consumers, because they are capable of correcting skin discoloration.

Depending on the consumers' taste and/or the degree of skin imperfections and/or the skin tonal variations and/or the skin discoloration surrounding the eyes, a high coverage effect may be desired and/or needed. A high coverage effect may be obtained by incorporating a high proportion of pigments, especially pigmentary grade titanium dioxide particles, into the cosmetic compositions. Application onto the skin of a composition providing high coverage, however, usually impairs the natural appearance of the skin. In particular, the application onto the skin of a composition providing high coverage usually results in a white hue across the skin. The white hue is also known as "chalkiness" for consumers having darker skins and "pastiness" for consumers having lighter skins. There is a need, therefore, to provide a cosmetic composition providing high coverage, particularly for masking skin imperfections and/or tonal variations of the skin, while retaining a natural skin appearance. There also is a need to provide a cosmetic composition correcting the skin discoloration surrounding the eyes, while retaining a natural skin appearance. There also is a need to provide a cosmetic composition which delivers high coverage whilst imparting a minimal white hue (ghost-like, doll-like effect) to the skin, or even whilst imparting no white hue to the skin. There also is a need to provide a cosmetic composition which delivers high coverage to darker skin whilst imparting minimal chalkiness, or even whilst imparting no chalkiness. There also is a need to provide a cosmetic composition which delivers high coverage to lighter skin whilst imparting minimal pastiness, or even whilst imparting no pastiness. Finally, there is a need to provide a cosmetic composition that delivers high coverage to the skin, and that minimizes further the white hue to the skin, compared to currently marketed cosmetic compositions.

Chalkiness and/or pastiness, i.e. the white hue across the skin, and more generally an unnatural appearance of the skin, is generally associated with the reflectance angle of light. When using conventional titanium dioxide, there is a specular reflection observed. This undesirable effect may be reduced by incorporating a lower proportion of pigmentary grade titanium dioxide particles into the cosmetic compositions, but doing that has the disadvantage of reducing the coverage provided to the skin. There is a need, therefore, to provide a cosmetic composition that provides high coverage of skin while minimizing the specular reflection.

The use of aluminum hydroxide powder in cosmetic compositions is known. Typically, the compositions include aluminum hydroxide deposited on the surface of a powder as a coating, as described for example, in U.S. Pat. Nos. 4,084,983, 4,323,554, 4,309,480, 4,968,351, 5,156,889, 6,416,573, 6,531,524, 6,630,019, 7,531,184, and U.S. Patent Application Publication No. 2001/0005735, the disclosures of each of which are incorporated by reference herein in their entireties. It also has been known to use alumina, not aluminum hydroxide, as a powder particle, and coat the alumina at least partially with titanium dioxide (JP 2008-088317), or phosphoric acid or phosphate (U.S. Pat. No. 6,015,456). It also has been described in U.S. Pat. No. 7,682,604 to provide a composite powder useful in cosmetic compositions in which a flaky substrate powder (e.g., mica) is contacted with a seed particle that acts as nuclei on the surface of the flaky substrate to grow barium sulfate particles or zinc oxide particles. Seed particles include titanium oxide, zinc oxide, alumina, aluminum hydroxide, silica, and iron oxide.

Accordingly, what is needed in the art is a pigment that can be used in cosmetic systems without using a significant amount of emulsifiers.

BRIEF SUMMARY

According to a first aspect, an embodiment relates to a cosmetic composition comprising pigment-containing aluminum hydroxide particles having an average coated ratio from about 20% to about 100% pigment by weight of the aluminum hydroxide and, a cosmetically acceptable carrier. The aluminum hydroxide particles serve as the base and are coated with, or have contained on the surface thereof, at least one pigment. This composition may be suitable for providing high coverage while minimizing the specular reflection.

According to another feature of an embodiment, there is provided a method of making pigment-containing aluminum hydroxide particles that comprises preparing an aqueous sodium hydroxide (NaOH aq) solution, adding at least one pigment to the solution with high speed to homogenize the mixture to a homogenized pigment mixture that is uniformly dispersed. The homogenized pigment mixture then is contacted with an aqueous aluminum sulfate ($Al_2(SO_4)_3$) solution with high speed. The method further includes filtering and drying the pigment to produce aluminum hydroxide particles coated with pigment.

According to another feature of an embodiment, there is provided pigment-containing aluminum hydroxide particles having an average coated ratio from 20% to 100% pigment by weight of the aluminum hydroxide for use as colorants in cosmetic compositions. Specifically, the pigment-containing aluminum hydroxide particles are present in an amount of from about 1% to about 75%, by weight of the composition.

BRIEF DESCRIPTION OF THE DRAWINGS

FIG. 1 is a collection of samples showing a comparison between the inventive pigments and comparative pigments.

DETAILED DESCRIPTION OF THE INVENTION

This invention relates to a powder that comprises aluminum hydroxide as the substrate coated with at least one pigment, in which the aluminum hydroxide substrate has an average coated ratio from 20% to 100% pigment by weight of the aluminum hydroxide particles. The aluminum hydroxide coated with the at least one pigment may be useful in cosmetic formulations together with a cosmetically acceptable carrier. While it is possible to use the pigment in cosmetic formulations, and especially as a foundation formulation, the pigment also may be useful in inks, paints, varnishes, toners, sunscreen formulations, and the like.

The following definitions and non-limiting guidelines must be considered in reviewing the description of this invention set forth herein. The headings (such as "Background" and "Brief Summary,") and sub-headings used herein are intended only for general organization of topics within the disclosure of the invention, and are not intended to limit the disclosure of the invention or any aspect thereof. In particular, subject matter disclosed in the "Background" may include aspects of technology within the scope of the invention, and may not constitute a recitation of prior art. Subject matter disclosed in the "Brief Summary" is not an exhaustive or complete disclosure of the entire scope of the invention or any embodiments thereof. Classification or discussion of a material within a section of this specification as having a particular utility (e.g., as being an "active" or a "carrier" ingredient) is made for convenience, and no inference should be drawn that the material must necessarily or solely function in accordance with its classification herein when it is used in any given composition.

The citation of references herein does not constitute an admission that those references are prior art or have any relevance to the patentability of the invention disclosed herein. Any discussion of the content of references cited in the Background is intended merely to provide a general summary of assertions made by the authors of the references, and does not constitute an admission as to the accuracy of the content of such references.

The description and specific examples, while indicating embodiments of the invention, are intended for purposes of illustration only and are not intended to limit the scope of the invention. Moreover, recitation of multiple embodiments having stated features is not intended to exclude other embodiments having additional features, or other embodiments incorporating different combinations the stated of features. Examples are provided for illustrative purposes of how to make and use the compositions and methods of this invention and, unless explicitly stated otherwise, are not intended to be a representation that given embodiments of this invention have, or have not, been made or tested.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention. In addition, the compositions and the methods may comprise, consist essentially of, or consist of the elements described therein.

As used throughout, ranges are used as a shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Throughout this description, the use of the term "about" or "approximately" is intended to denote an approximation of the number, which includes the number modified by the term, and a reasonable deviation from that term, including standard measurement errors. Unless otherwise specified, all percentages and amounts expressed herein and elsewhere in the specification should be understood to refer to percentages by weight. The amounts given are based on the active weight of the material. The recitation of a specific value herein is intended to denote that value, plus or minus a degree of variability to account for errors in measurements. For example, an amount of 10% or about 10% may include 9.5% or 10.5%, given the degree of error in measurement that will be appreciated and understood by those having ordinary skill in the art.

As used herein, the term "cosmetic composition" means a composition that is intended to be applied onto the consumer's skin, particularly onto the facial skin or onto the body skin area or onto hair, so as to regulate the condition of the skin and/or to improve the appearance of the skin. The term "powder" means any insoluble material having a particle size within the range of from about 0.01 micrometer to about 50 micrometers. The term "average primary particle size" of pigment-containing aluminum hydroxide particles means the equivalent volume mean primary particle size of the elementary pigment-containing aluminum hydroxide crystals. The average primary particle size is measured on the pigment-containing aluminum hydroxide particles.

Throughout this description, the term "foundation" means a cosmetic composition that is intended to be applied onto the consumer's skin, particularly, onto the facial skin, body skin and hair so as to provide coverage and/or to mask skin irregularities and/or skin imperfections and/or skin tonal variations. The term "chalkiness" means the white hue which is observed onto skin after applying onto skin, particularly darker skin, a cosmetic composition providing high coverage. The term "pastiness" means the white hue that may be observed on the skin after applying onto skin, particularly lighter skin, a cosmetic composition providing high coverage.

All percentages, ratios and proportions herein are by weight, unless otherwise specified. All such weights as they pertain to listed ingredients are based on the active level, unless otherwise specified.

Embodiments of the invention include cosmetic compositions that contain aluminum hydroxide particle substrates coated with a pigment in which the coated pigment is present in an amount of from about 20% to 100% of coating by weight of the aluminum hydroxide. In one embodiment, the pigment is present in an amount of from about 25% to about 75% of pigment by weight of the aluminum hydroxide, and in another embodiment, the pigment is present in an amount of about 50% of pigment by weight of the aluminum hydroxide.

The pigments useful in the embodiments include any known pigment that is capable of forming a powder coating on an aluminum hydroxide particle in the coating ratios described herein. Suitable pigments include, for example, inorganic white pigments such as titanium dioxide and zinc oxide, inorganic red system pigments such as iron oxide (red iron oxide) and titanic acid irons, inorganic brown system pigments such as γ-iron oxides, inorganic yellow system pigments such as yellow soil and yellow iron oxides, inorganic black color system pigments such as tetravalent acid iron oxide, carbon black, inorganic violet system pigments such as mango violet, cobalt violet, inorganic green system pigments such as chromium oxide, chromium hydroxide, and titanic acid cobalt, inorganic blue system pigments such as ultramarine blue, and prussian blue, pearl pigments such as titanium dioxide covered mica, titanium dioxide covered bismuth oxychloride, bismuth oxychloride, titanium dioxide covered talc, fish scale foil, colored titanium dioxide covered mica, metal powder pigment such as aluminum powder, copper powder, colored composite pigments such as iron-doped zinc oxide and iron-doped titanium dioxide.

Other pigments may be used, such as red No. 201, red No. 202, red No. 204, red No. 205, red No. 220, red No. 226, red No. 228, red No. 405, AP2199 Iron Oxide HP (commercially available from Elementis, Hightstown, N.J.), orange-colored No. 203, orange-colored No. 204, yellow No. 205, yellow No. 401 and blue No. 404, organic chlorophyll pigment such as FD&C Red No. 3, red No. 104, red No. 106, red No. 227, red No. 230, red No. 401, red No. 505, orange-colored No. 205, FD&C Yellow No. 4, yellow No. 5, yellow No. 202, yellow No. 203, orange-colored No. 3 and zirconium, barium, or aluminum lake of blue No. 1, natural colorants such as β-carotene, hydrocarbon oils such as squalane, mineral oil, vaseline, micro crystalline wax, ozokerite, ceresin, myristic acid, palmitic acid, stearic acid, oleic acid, iso-stearic acid, cetyl alcohol, hexadecyl alcohol, oleyl alcohol, cetyl 2-ethylhexanoate, 2-ethylhexyl palmitate, 2-octyldodecyl myristate, neo-pentylglycol di-2-ethylhexanoate, glyceryl tri-2-ethylhexanoate, 2-octyldocyl oleate, isopropyl myristate, glyceryl triisostearate, caprylic/capric triglyceride, olive oil, avocado oil, yellow bees wax, myristyl myristate, mink oil, lanolin oil, silicone oil, higher fatty acid oil, ester oils of fatty acids, higher alcohol, oil components of wax groups, cyclopentasiloxanes, dimethicones, trimethylsiloxysilicates, and organic solvents such as acetone, toluene, butyl acetate, and ester acetate can be used in various amounts. At least one pigment can be used to coat an aluminum hydroxide particle, or combinations of two or more, or three or more pigments may be used. In addition, cosmetic compositions may contain multiple pigments of varying shades, at least one of which, and optionally, all of which are aluminum hydroxide coated with at least one pigment as described herein.

The average particle size of the pigment particles that form a coating on the aluminum hydroxide substrates can be within the range of from about 0.01 to about 75 µm, more preferably from about 0.05 to about 65, even more preferably from about 0.1 to about 50 µm, and most preferably from about 1 to about 25 µm. The average thickness of the pigment may be within the range of from about 0.01 to about 3 µm, more preferably from about 0.1 to about 2, and most preferably from about 0.1 to about 1.5 µm. In an embodiment, the pigment material may have a refractive index within the range of from about 1.25 to about 1.95, more preferably from about 1.40 to about 1.80, and most preferably from about 1.45.about. 1.65.

Powder materials also may be utilized in accordance with the embodiments, and include any powder useful in cosmetic compositions including those that provide one or more of the following effects: luster effect, oil absorption, feeling improvement, cover effect, and the like. The particular powder used is not critical, and powders need not be used in various embodiments. Suitable powders include, for example, those belonging to the clay mineral group: such as those containing illite groups such as sericite (silky mica), muscovite, biotite, lithia mica, and synthetic mica; those containing kaolin groups such as kaolionite, nacrite, dekkite, halloysite; those containing sillimanite groups such as sillimanite and kyanite; magnesium silicate systems such as talc, and serpentine groups; and titanium dioxide and zinc dioxide. A single powder may be used to coat the aluminum hydroxide substrate, or combinations of powders may be used to specifically tailor the powder-containing aluminum hydroxide.

Like the pigment powders described above, the average particle size of the powder particles can be within the range of from about 0.01 to about 75 µm, more preferably from about 0.05 to about 65, even more preferably from about 0.1 to about 50 µm, and most preferably from about 1 to about 25 µm. The average thickness of the powder may be within the range of from about 0.01 to about 3 µm, more preferably from about 0.1 to about 2, and most preferably from about 0.1 to about 1.5 µm. In an embodiment, the powder material may have a refractive index within the range of from about 1.25 to about 1.95, more preferably from about 1.40 to about 1.80, and most preferably from about 1.45.about. 1.65.

The refractive index of oil solutions that are usually used in cosmetics typically is within the range of from about 1.39 to about 1.51, while the refractive index of mica is 1.59 and talc is 1.53, and the refractive index of the stratum corneum is 1.55. As can be seen from the numbers above, when normal pigments are used in cosmetics, the refractive indicies are very similar to each other, and when the pigments are wetted with skin-secreted sebum at its oil absorption or over this amount, some of the materials that make up the cosmetic film on the skin become transparent. When an excess amount of sebum is secreted, a reflection from the surface of the sebum film, as well as the reflection from the surface of the material dispersed within the sebum, will emphasize and create an undesirable shine, that when viewed from different angles will make the wrinkles stand out, and in occasion make the wearer of the cosmetic have a very tired look. By forming the aluminum hydroxide substrate coated with the pigment in accordance with the embodiments, the shine can be reduced significantly, and the resulting pigment has improved specular reflection and reflection strength.

The final pigment comprised of the aluminum hydroxide particles coated with the pigment may have an average particle size within the range of from about 0.01 to about 50 µm, and in some embodiments the average particle size can be within the range of from about 0.1 to about 45 µm, and in other embodiments, the average particle size can be within the range of from about 1 to about 35 µm. The pigment can be useful in a cosmetic composition to provide a high coverage of skin while retaining a natural skin appearance, and can be used in such a composition in an amount of from about 1 to about 75% by weight. The inventors have found the significantly less pigment can be used to provide the same coloring effect, when the pigment has been contacted with aluminum hydroxide to form an aluminum hydroxide substrate coated with pigment powder, including up to about 75% less pigment to achieve the same color coverage, when compared to an untreated pigment, or up to about 50% less pigment, or up to about 25% less pigment. In other embodiments, the pigment-containing aluminum hydroxide can be used in an amount of from about 0.5 to about 65% by weight, in other embodiments from about 1 to about 50% by weight, and in yet other embodiments, from about 1 to about 30% by weight.

Depending on the formulation (e.g., liquid formulation, powder formulation, skin lotion, body soap, etc.), the amount of the pigment can vary widely. For example, for a liquid formulation, the amount of the aluminum hydroxide coated with pigment can be used in an amount of from about 0.5 to about 5% by weight, or from about 0.75 to about 3.5% by weight, or from about 1 to about 2.5% by weight, or at about 1% by weight. For a powder formulation, such as makeup foundation or the like, the amount of the aluminum hydroxide coated with pigment can be used in an amount of from about 5 to about 65% by weight, or from about 10 to about 40% by weight, or from about 15 to about 35% by weight, or at about 20% by weight. For a skin lotion formulation, the amount of the aluminum hydroxide coated with pigment can be used in an amount of from about 0 to about 30% by weight, depending on whether color is desired, or from about 0.5 to about 20% by weight, or from about 1 to about 10% by weight. For a body soap formulation, the amount of the aluminum hydroxide coated with pigment can be used in an amount of from about 0 to about 30% by weight, depending on whether color is desired, or from about 0.5 to about 20% by weight, or from about 1 to about 10% by weight.

The cosmetic compositions useful in the embodiments described herein also may contain other conventional components useful in various cosmetic compositions. Any cosmetically acceptable vehicle may be used together with the aluminum hydroxide coated with the pigment powder. Such vehicles may include, for example, water, glycerin, dimethicone, beeswax, glyceryl stearate, and the like. Other ingredients normally used in cosmetics also may be present, when desired. For example, inorganic powders such as talc, kaolin, sericite, muscovite, phlogopite, red mica, biotite, synthetic mica, lithia mica, vermiculite, magnesium carbonate, calcium carbonate, diatomite, magnesium silicate, calcium silicate, aluminum silicate, barium silicate, barium sulfate, strontium silicate, wolframic acid metal salt, or silica, hydroxyapatite, zeolite, boron nitride, ceramic powder, organic powders such as nylon powder, polyethylene powder, polystyrene powder, benzoguanamine powder, polyfluoridation ethylene powder, di-styrene benzene polymer powder, epoxy powder, acrylic powder, silicone powder, microcrystalline cellulose, Resins such as alkyd resin, urea-formaldehyde resin, Nylon-12, plasticizers such as camphor, acetyl tributyl citric acid, ultraviolet absorbing agents, antioxidants, antiseptics, surfactants, moisturizing agents, perfumes, water, alcohol, and thickeners can also be used.

The powder aluminum hydroxide coated with at least one pigment can be prepared by preparing an aqueous sodium hydroxide (NaOH aq) solution, adding at least one pigment to the solution with high speed to homogenize the mixture to form a homogenized pigment mixture that is uniformly dispersed. One or more pigments may be added, wherein multiple pigments can be used. The pigments can be added as a powder, solution, emulsion, gel, and in one embodiment, the at least one pigment is in the form of a powder. The homogenized pigment mixture (containing one or more pigments) then can be contacted with an aqueous aluminum sulfate ($Al_2(SO_4)_3$) solution with high speed. The method further includes filtering and drying the pigment material to produce aluminum hydroxide particles coated with pigment, which typically is in the form of a powder.

In one embodiment, the aqueous sodium hydroxide solution and the aqueous aluminum sulfate solutions are prepared as pre-mixes and then the method is carried out by first adding at least one pigment powder (or optionally at least one pigment solution or emulsion, or liquid containing at least one pigment) to the aqueous sodium hydroxide pre-mix. The pre-mix with the added pigment (or pigments) then can be homogenized in a stirred reactor, or homogenizer apparatus using any conventional apparatus to homogenize the mixture. In one embodiment, the mixture is homogenized and the temperature is increased to within a range of from about 30 to about 75° C., or within a range of from about 40 to about 60° C., or to about 50° C. After the mixture is homogenized and the temperature achieved, the aqueous aluminum sulfate pre-mix can be added with continuous homogenization. In one embodiment, the aqueous aluminum sulfate pre-mix is added step-wise using any mechanism capable of metering in the solution (e.g., pump, valve, titration, etc.) until the pH of the mixture reaches a value within the range of from about 5.5 to about 8.5, or until the pH of the mixture reaches a value within the range of from about 6.5 to about 7.5, or until the pH of the mixture reaches about 7.0.

The resulting mixture should contain aluminum hydroxide substrate particles, coated with the at least one pigment. The particles then can be separated from the mixture using any known mechanism capable of filtering the particles from the mixture, including for example, conventional filter paper, filter press, or other known filtering apparatus. The particles separated by filtration then can be dried using any known mechanism capable of drying particles, including kiln or oven drying, passing the particles through a heated oven or press, spray drying, and the like. Drying can take place for a period of time from about 1 hour to about 30 hours, or from about 5 hours to about 20 hours, or from about 12 hours to about 18 hours, or about 16 hours, depending on the drying temperature. The drying temperature may be within the range of from about 75° C. to about 175° C., or from about 90° C. to about 120° C., or about 105° C. The final dried particles comprise aluminum hydroxide powder substrates, coated with the pigment.

In one embodiment, water and sodium hydroxide may be mixed to form a first pre-mix, in which the amount of aqueous sodium hydroxide solution is from about 125 to about 185% by weight based on the weight of the at least one pigment, or from about 145 to about 175% by weight based on the weight of the at least one pigment, or from about 160% by weight based on the weight of the at least one pigment. Water and aluminum sulfate also may be mixed to form a second pre-mix, in which the amount of aqueous sodium hydroxide solution is from about 185 to about 225% by weight based on the weight of the at least one pigment, or from about 195 to about 215% by weight based on the weight of the at least one pigment, or from about 200% by weight, based on the weight of the at least one pigment.

In accordance with an embodiment, at least one pigment, such as iron oxide, titanium dioxide, zinc dioxide, carbon black, etc., or combinations thereof, may be added to the first pre-mix, and the resulting mixture homogenized and the temperature increased as stated above. The second pre-mix then may be added to the homogenized mixture containing the at least one pigment in a step-wise manner until the pH reaches a value as described previously. The resulting particles then can be filtered and dried as discussed above.

The method can be carried out in a batch or continuous process to produce the powder particles comprised of an aluminum hydroxide substrate coated with at least one pigment in an amount of from about 20% to 100% of pigment coating by weight of the aluminum hydroxide. The term "coating" or "coated" is not meant to denote a uniform distribution of pigment over the entire surface. Rather, the particles of pigment may adhere to the surface of the aluminum hydroxide substrate and do not necessarily coat the entire surface, although in some embodiments, the pigment can be adhered over the entire surface of the aluminum hydroxide substrate. In some embodiments, the pigment adheres to about 10 to about 95% of the surface, or from about 20 to about 80%, or from about 30 to about 70%, or from about 40 to about 65% of the surface of the aluminum hydroxide.

The aluminum hydroxide particles that are coated with the at least one pigment can be used in cosmetic compositions, together with a cosmetically acceptable carrier. The formulation of the particular cosmetic formulation, or other product, can be carried out using conventional techniques. The inventors have discovered that the aluminum hydroxide particles coated with the at least one pigment have strong color forming capabilities, allowing less pigment to be used. Typically, a large amount of pigment may be needed in some cosmetic formulations to provide a strong color, but the additional amount of pigment may result in poor Chroma, and cosmetics containing high amounts of pigments provide an inferior feel when applied to the skin. The aluminum hydroxide particles coated with at least one pigment show an improvement in color, when measured using the CIE LAB color scale, of anywhere from about 10% to about 70% stronger color, when compared to an untreated pigment. For example, the value of a* in the CIE LAB color scale measures the strength of red. For red pigments, the aluminum hydroxide particles coated with a red pigment, or at least one red pigment, can show an increase in the value of a* of from about 10% to about 70%, or from about 25% to about 45%, or in an increase of about 40%, when compared to the value of a* for the same red pigment that has not been treated in accordance with the embodiments.

The aluminum hydroxide particles coated with a pigment show an improvement in color, when measured using the CIE LAB color scale, of anywhere from about 10% to about 100% stronger color, when compared to the same pigment treated with conventional treatment agents, such as lecithin, amino acids, silicone, or metal soaps. For example, the value of a* in the CIE LAB color scale measures the strength of red. For red pigments, the aluminum hydroxide particles coated with a red pigment, or at least one red pigment, can show an increase in the value of a* of from about 10% to about 100%, or from about 25% to about 85%, or in an increase of up to about 70%, when compared to the value of a* for the same red pigment that has been treated with conventional treatment agents.

While the aluminum hydroxide particles coated with the at least one pigment are particularly useful in cosmetic compositions, there are no restrictions to the form of cosmetics in which the particles can be used. For example the particles can be used in several forms such as powder form, cake form, pencil and stick form, pellet form, ointment form, liquid form, milky lotion form, or cream form. The particles can also be used in various other fields besides cosmetics, such as for industrial purposes, such as inks, paints (coating), plastics, rubber additives, rubber moldings, rubber mold separating material etc., and other various lubricants.

The aluminum hydroxide particles coated with at least one pigment may be used in cosmetic products, such as foundations, lip sticks, eye shadow, lotions, creams, concealer, blush, eyeliners, mascara, eyebrow liner, lipliner, and sunscreen. They may also be used in toiletry products, such as deodorants, antiperspirants, body soaps, and shower gels. When the particles are used in a cosmetic product or a toiletry product, other typical components used in making the cosmetic product or toiletry product can be added to the at least one pigment-containing aluminum oxide. For instance, lip stick will often contain various oils and waxes in addition to the pigments. The pigment particles may be used with other powders, pigments, or other components, including the same pigment or different pigment(s) adhered to the aluminum hydroxide substrate, but added separately.

The following examples are intended to illustrate the invention. These examples should not be used to limit the scope of the invention, which is defined by the claims.

EXAMPLE 1

Preparation of Aluminum Hydroxide Particle Coated With Red Iron Oxide Pigment

An aqueous sodium hydroxide first pre-mix solution was prepared by mixing water and sodium hydroxide to form a first pre-mix in an amount of 160% of the amount of red iron oxide pigment powder added. An aqueous aluminum sulfate second pre-mix solution was prepared by mixing water and aluminum sulfate in an amount of 200% of the amount of iron oxide pigment powder added. Red iron oxide powder (AP2199 Iron Oxide HP, commercially available from Elementis, Hightstown, N.J.) was added to the first pre-mix, the mixture was homogenized in a high speed mixer, and the temperature was raised to 50° C. The second pre-mix then was added step-wise with a controlled pump to the homogenized and heated mixture containing the iron oxide pigment until the pH of the mixture reached 7.0. The resulting mixture then was filtered using a paper filter and the filter cake was dried in an oven for 16 hours at a temperature of 105° C. to prepare an aluminum hydroxide powder coated with red iron oxide in which the coating amount was 50% red iron oxide pigment, based on the weight of the aluminum hydroxide. The resulting pigment particles were comprised of aluminum hydroxide substrates coated with red iron oxide pigment particles.

EXAMPLE 2

Measurement of Coloring Capability and Comparison Examples

The aluminum hydroxide powder of Example 1 was compared to the same red iron oxide pigment in its native powder form as a control, and the same red iron oxide pigment treated with conventional treating agents. The conventional treating agents included treating the red iron oxide in the same manner as in Example 1, but instead of aluminum sulfate, the solution contained lecithin as one comparison, or acyl glutamic acid as another comparison, or with dimethicone as another comparison, or with myristic acid (potassium myristate) as another comparison. The particles containing red iron oxide pigments prepared in accordance with Example 1, the native red iron oxide pigment control, and the comparative samples, all were placed on double sided tape (2 cm×5 cm) in an amount of about 2.6 mg, and then the color values (L*, a*, and b*) were measured using an X Rite ColorMunki. The results are shown in FIG. 1, and listed below in Table 1.

TABLE 1

Color Measurement

| Sample (treatment) | L* | a* | b* |
| --- | --- | --- | --- |
| Example 1 | 41.2 | 29.8 | 23.4 |
| Control | 39.6 | 21.7 | 12.9 |
| Lecithin | 36.4 | 17.6 | 10.8 |
| Acyl Glutamic Acid | 38.4 | 20.4 | 12.2 |
| Dimethicone | 38.0 | 18.5 | 8.8 |
| Myristic Acid | 17.2 | 19.8 | 11.8 |

As seen from the above table, the inventive sample provided a far greater degree of coloring in the red spectrum (measurement of a*), when compared to the same pigment that has not been treated, or when compared to the same pigment treated with conventional treating or coating agents. Specifically, the inventive example showed a strong red color having greater than 37% greater value of a*, when compared to the control, and having up to 70% greater value of a*, when compared to the same pigment treated with conventional treatment and coating agents. Accordingly, the aluminum hydroxide particles coated with the at least one pigment prepared in accordance with the embodiments provides an advantage over conventional pigments because far less pigment can be used to achieve the same coloring effect. Indeed, the example 1 particles only contained 50% of the pigment used in the control (the control was 100% pigment whereas Example 1 contained particles with 50% pigment), but had a far superior and stronger red color.

Thus, the embodiments include cosmetic formulations containing anywhere from about 15% to about 100% less pigment than an otherwise identical formulation that contains either the identical pigment but untreated, or the identical pigment but treated with conventional treating and coating agents. Other embodiments include cosmetic formulations containing from about 25% to about 75% less pigment, or from about 35% to about 65% less pigment, or from about 40% to about 60% less pigment, or about 50% less pigment than an otherwise identical formulation that contains either the identical pigment but untreated, or the identical pigment but treated with conventional treating and coating agents.

While the embodiments have been described with reference to specific examples and features, persons having ordinary skill in the art will appreciate that various modifications may be made to the embodiments without departing from the spirit and scope thereof.

What is claimed is:

1. A cosmetic composition comprising aluminum hydroxide particles coated with at least one pigment in an amount within the range of from about 20% to about 100% pigment by weight of the aluminum hydroxide, and a cosmetically acceptable carrier.

2. The cosmetic composition as claimed in claim 1, wherein the at least one pigment is selected from one or more of the group consisting of titanium dioxide, zinc oxide, iron oxide, titanic acid irons, γ-iron oxides, yellow soil, tetravalent acid iron oxide, carbon black, mango violet, cobalt violet, chromium oxide, chromium hydroxide, titanic acid cobalt, ultramarine blue, prussian blue, titanium dioxide covered mica, titanium dioxide covered bismuth oxychloride, bismuth oxychloride, titanium dioxide covered talc, fish scale foil, colored titanium dioxide covered mica, aluminum powder, copper powder, iron-doped zinc oxide, iron-doped titanium dioxide, and mixtures thereof.

3. The cosmetic composition as claimed in claim 1, wherein the at least one pigment is at least one iron oxide pigment.

4. The cosmetic composition as claimed in claim 1, wherein the at least one pigment is present in an amount of about 50%, based on the weight of the aluminum hydroxide.

5. The cosmetic composition as claimed in claim 1, wherein the aluminum hydroxide particles coated with at least one pigment have an average particles within the range of from about 0.01 to about 50 μm.

6. The cosmetic composition as claimed in claim 5, wherein the aluminum hydroxide particles coated with at least one pigment have an average particles within the range of from 1 to about 35 μm.

7. The cosmetic composition as claimed in claim 1, wherein the aluminum hydroxide particles coated with at least one pigment are present in the composition in an amount within the range of from about 1 to about 75% by weight.

8. The cosmetic compositions as claimed in claim 7, wherein the aluminum hydroxide particles coated with at least one pigment are present in the composition in an amount within the range of from about 1 to about 30% by weight.

9. The cosmetic composition as claimed in claim 1, further comprising at least one powder selected from the group consisting of sericite, muscovite, biotite, lithia mica, synthetic mica, kaolionite, nacrite, dekkite, halloysite, sillimanite, kyanite, talc, titanium dioxide, zinc dioxide, and mixtures thereof.

10. The cosmetic composition as claimed in claim 1, wherein the composition is selected from the group consisting of a foundations, lip stick, eye shadow, lotion, cream, concealer, blush, eyeliner, mascara, eyebrow liner, lipliner, sunscreen, deodorant, antiperspirant, body soap, and shower gel.

* * * * *